United States Patent [19]

Sammons et al.

[11] Patent Number: 5,676,849
[45] Date of Patent: Oct. 14, 1997

[54] METHOD FOR ENRICHMENT OF FETAL CELL POPULATION FROM MATERNAL WHOLE BLOOD SAMPLES

[75] Inventors: David W. Sammons; Michael Manley; Joseph G. Utermohlen; Garland E. Twitty, all of Tucson, Ariz.

[73] Assignee: BioSeparations, Inc., Tucson, Ariz.

[21] Appl. No.: 401,131

[22] Filed: Mar. 8, 1995

Related U.S. Application Data

[63] Continuation-in-part of Ser. No. 327,483, Oct. 21, 1994.

[51] Int. Cl.$^6$ .......................... G01N 27/26; G01N 33/49; B01D 21/26
[52] U.S. Cl. .......................... 210/806; 204/450; 204/518; 204/543; 210/660; 210/749; 210/767; 210/782; 210/787; 210/789; 424/533; 424/720; 435/2; 436/174; 436/175; 436/177; 436/178; 530/412; 530/413; 530/417; 530/427
[58] Field of Search .......................... 210/660, 748, 210/749, 754, 767, 782, 787, 789, 515, 516, 806; 435/2, 803; 424/720, 93 W, 533, 93.73; 436/174, 175, 177, 178; 530/413, 415, 417, 427, 412; 204/299 R, 301, 180.1, 450, 456, 457, 488, 518, 543, 544

[56] References Cited

U.S. PATENT DOCUMENTS

| | | | |
|---|---|---|---|
| 3,829,370 | 8/1974 | Bourat. | |
| 3,989,613 | 11/1976 | Gritzner | 204/301 |
| 4,185,964 | 1/1980 | Lancaster | 424/11 |
| 4,204,929 | 5/1980 | Bier | 204/301 |
| 4,323,439 | 4/1982 | O'Farrell | 204/299 R |
| 4,362,612 | 12/1982 | Bier | 204/301 |
| 4,588,492 | 5/1986 | Bier | 204/301 |
| 4,673,483 | 6/1987 | Mandle | 204/301 |
| 4,925,572 | 5/1990 | Pall | 210/767 |
| 4,963,236 | 10/1990 | Rodkey et al. | 204/183.2 |
| 5,173,164 | 12/1992 | Egen et al. | 204/301 |
| 5,192,553 | 3/1993 | Boyse et al. | 435/2 |
| 5,336,387 | 8/1994 | Egen et al. | 204/301 |
| 5,432,054 | 7/1995 | Saunders et al. | 435/2 |

FOREIGN PATENT DOCUMENTS

PCT/US94/00644  1/1994  WIPO.

OTHER PUBLICATIONS

Ivory, Cornelius F. and Gobie, William A., Continuous Counteracting Chromatographic Electrophoresis, *Biotechnology Prog.*, vol. 6, pp. 21-32, 1990.

Egen, N.B., Twitty, G.E., Thormann, W., and Bier, M., Fluid Stabilization during Isoelectric Focusing in Cylindrical and Annular Col., *Separation Science and Technology*, vol. 22(5), pp. 1383-1403, 1987.

"Fetal Cells in Materials Blood: Prospects for Noninvassive Prenatal Diagnosis" by Joe Leigh Simpson and Sherman Elias, *Annals of the New York Academy of Sciences* vol. 731 (Complete Book), pp. 1-270, (1994).

"Separation of pluripotent haematopoietic stem cells from spleen colony—forming cells" *Nature* vol. 347:188-189 (Sep. 13, 1990).

"Circulation of CD34 Hematopoietic Stem Cells in the Peripheral Blood of High-Dose Cyclophosphamide-Treated Patients: Enhancement by Intravenous Recombinant Human Granulocyte-Macrophage Colony-Stimulating Factor" by S. Siena, M. Bregni, B. Brando, F. Ravagnani, G. Bonadonna, and A. M. Gianni, *Blood*, vol. 74, No. 6: 1905-1914, (Nov. 1989).

(List continued on next page.)

*Primary Examiner*—John Kim
*Attorney, Agent, or Firm*—David G. Rosenbaum

[57] ABSTRACT

A method for enriching rare cell populations from a whole blood sample by separating rare cell fractions from whole according to the relative charge density and/or the relative binding affinity for a leukocyte depletion solid phase matrix. The enrichment method may be operated stand alone, or as a pre or post-processing step in conjunction with a charge-flow separation method.

10 Claims, 8 Drawing Sheets

OTHER PUBLICATIONS

"Transplantation with Blood Stem Cells" by A. Zander, J. Lyding, and S. Bielack, *Blood Cells*, vol. 17: 301–309 (1991).

"Circulating Exteropoietic Precursors in Human Blood" by M. Ogawa and J. Sexton, *Clinical Research*, vol. 24: 316A, (1976).

"Characterization of an erythroid precursor cell of high proliferative capacity in normal human peripheral blood" by B. Clarke and D. Housman, *Proc. Natl. Acad. Sci. USA*, vol. 74, No. 3: 1105–1109 (Mar. 1977).

"Purification and Characterization of Mouse Hematopoietic Stem Cells" by G. Spangrude, S. Heimfeld, I. Weissman, *Science*, vol. 58–62, (1988).

"Antigen CD34 Marrow Cells Engraft Lethally Irradiated Baboons" by Ronald J. Berenson, et al., *J. Clin. Invest.*, vol. 81: 951–955, (1988).

"Treatment of Aggressive Multiple Myeloma by High–Dose Chemotherapy and Total Body Irradiation Followed by Blood Stem Cells Autologous Graft" by Jean–Paul Fermand, Yves Levy, Jean Gerota, Marc Benbunan, Jean Marc Cosset, Sylvia Cataigne, Maxime Siligmann and Jean–Claude Brouet, *Blood*, vol. 73, No. 1: 20–23 (Jan. 1989).

"Normal Blood Cell Values in the Early Mid Trimester Fetus" by D.S. Millar, L.R. Davis, C.H. Rodeck, K.H. Nicolaides and R.S. Mibashan, *Prenatal Diagnosis*, vol. 5: 367–373 (1985).

"Human umbilical cord blood as a potential source of transplantable hematopoietic stem/progenitor cells" by H. Broxmeyer, G. Douglas, G. Hangoc, S. Cooper, J. Bark, D. English, M. Arny, L. Thomas and E. Boyse, *Proc. Natl. Acad. Sci. USA* vol. 86: 3828–3832 (May 1989).

"Enrichment of Erythrocytes of Fetal Origin From Adult–Fetal Blood Mixtyres via Selective Hemolysis of Adult Blood Cells: An Aid to Antenatal Diagnosis of Hemoglobinopathies" by S. Boyer, A. Noyes and M. Boyer, *Blood, The Journal of The American Society of Hematology*, vol. 47, No. 6: 883–897, (Jun. 1976).

"Carbonic anhydrases from human neonatal erythrocytes" by J. Sell and H. Peterixg, *J. Lab Clin Med*, vol. 84: 369–377, (1974).

"Concentration of Fetal Red Blood Cells from a Mixture of Maternal and Fetal Blood by Anti–i of Hemoglobinopathies" by Y.W. Kan, D.G. Nathan, G. Cividalli, M.C. Crookston, *Blood*, vol. 43, No. 3:411–415, (Mar. 1974).

"Carbonic Anhydrase I is an Early Specific Marker of Normal Human Erythroid Differentiation" by J.L. Villeval, et al., *Blood*, vol. 66, No. 5: 1162–1170, (Nov. 1985).

"Exploratory Studies on Detection of Hemoglobins in the Early Human Fetus In Utero" by V. Heading, et al., *Annals of the New York Academy of Sciences*, vol. 241: 715–721 (1974).

"Immunological Basis for Detection of Sickle Cell Hemoglobin Phenotypes in Amniotic Fluid Erythrocytes" by S. Boyer, M. Boyer, A. Noyes and T. Belding, *Annals of the New York Academy of Sciences*, vol. 241: 699–713 (1974).

"Colony Formation of Clone–Sorted Human Hematopoietic Progenitors" By H. Ema, T. Suda, Y. Mura, and H. Nakauchi, *Blood*, vol. 75, No. 10: 1941–1946, (May 1990).

"Developmental Hemopoiesis" by W.G. Wood, pp. 75–98 (undated).

"Blast Cell Colony Assay for Umbilical Cord Blood and Adult Bone Marrow Progenitors" by A. Leary and M. Ogawa, *Blood*, vol. 69, No. 3: 953–956, (Mar. 1987).

"Fetal plasma erythropoietin concentration in red blood cell–isoimmunized pregnancies" by B. Thilaganthan, et al., *Am J Obstet Gynecol*, vol. 167: 1292–1297, (Nov. 1992).

"The Role of M–CSF and GM–CSF in Fostering Placental Growth, Fetal Growth, and Fetal Survival" by T. G. Wegmann, et al., *Transplantation Proceedings*, vol. 21, No. 1: 566–568, (Feb. 1989).

"Erythroblastosis and reticulocytosis in anemic fetuses" by K.H. Nicosides, et al., *Am J Obstet Gynecol*, vol. 21, No. 1: 1063–1065 (Nov. 1989).

"SFL 23.6: A Monoclonal Antibody Reactive With CFU–E, Erythroblasts, and Erythrocytes" by A. Gupta, et al., *Blood*, vol. 66, No. 3: 522–526, (1985).

"Erythroid Progenitors Forming Clusters In Vitro Demonstrate High Erythropoietin Sensitivity" by P. Lynn Ouellette and Frances C. Monette, *Journal of Cellular Physiology*, vol. 105: 181–184 (1980).

"The Production of Myeloid Blood Cells and Their Regulation During Health and Disease" by Hal E. Broxmeyer and Douglas E. Williams, *Crit Rev. Oncol Hemat*, vol. 8, No. 3: 173–226, (1988).

"Rapid chromosomes analysis with use of spontaneously dividing cells derived from umbilical cord blood (fetal and neonatal)" by Robert E. Tipton, et al., *Amer. J. Obstet and Gynecol*, vol. 161: 1546–1548, (1989).

"Isolation and Characterization of the CD34 Hematopoietic Progenitor Cells from the Peripheral Blood of Patients with Chronic Myeloid Leukemia" by F. Silvestri, et al., *International Journal of Cell Cloning*, vol. 9: 474–490, (1991).

"Effects of Recombinant Human G–CSF, GM–CSF, IL–3, and IL–1α on the Growth of Purified Human Peripheral Blood Progenitors" by Y. Takaue, et al., *Blood*, vol. 76, No. 2: 330–335 (Jul. 15, 1990).

"Physical Separation of Hemopoietic Stem Cells from Cells Forming Colonies in Culture" by R.G. Worton, et al., *Cell. Physiol*, vol. 74: 171–182, (1969).

"Stimulation of fetal hemoglobin synthesis in bone marrow cultures from adult individuals" by Th. Papayannopoulou, et al., *Proc. Natl. Acad. Sci. USA*, vol. 73, No. 6:2033–2037, (1976).

"Human Marrow Erythropoiesis in Culture: II. Heterogeneity in the Morphology, Time Course of Colony Formation, and Sedimentation Velocities of the Colony–Forming Cells" by Makio Ogawa, et al., *American Journal of Hematology*, vol. 3: 29–36, (1977).

"'Pure' Human Hematopoietic Progenitors: Permissive Action of Basic Fibroblast Growth Factor" by M. Gabbianelli, et al., *Science* vol. 249: 1561–1564, (1990).

"Human Mononuclear Phagocyte Differentiation Antigens" by AI Dimitriu–Bona, et al., *The Journal of Immunology*, vol. 130: 145–152, (1983).

"Flow Cytometeric Analysis of Human Bone Marrow: I. Normal Erythroid Development" by Michael R. Loken, et al., *Blood*, vol. 69, No. 1: 255–263, (1987).

"Fetal cells in the maternal circulation: isolation by multiparameter flow cytometry and conformation by polymerase chain reaction" by Stephen Wachtel, et al., *Human Reproduction*, vol. 6, No. 10: 1466–1469, (1991).

"Expression of cell–surface HLA–DR, HLA–ABC and glycophorin during erythroid differentiation" by J. Robinson, et al., *Nature*, vol. 289: 68–71, (1981).

"Isolation of human haematopoietic progenitor cells using monclonal antibodies" by P.C.L. Beverley, et al., *Nature*, vol. 287: 332–333, (1980).

"Changes in Cell Surface Antigen Expression During Hemopoietic Differentiation" by C. Sieff, et al., *Blood*, vol. 60, No. 3: 703–713, (1982).

"Fetal nucleated cells in maternal peripheral blood: frequency and relationship to gestational age" by Hiromi Hamada, et al., *Human Genetics*, vol. 9: 427–432, (1993).

"Monoclonal Antibodies Detecting Antigenic Determinants With Restricted Expression on Erythroid Cells: From the Erythroid Committed Progenitor Level to the Mature Erythroblast" by T. Yokochi, et al., *Blood*, vol. 63, No. 6: 1376–1384, (Jun. 1984).

"Neonatal Hematology—Chapter 2: The Erythrocyte and its Disorders" by Frank A. Oski, *Hematology of Infancy and Childhood*, pp. 16–18, (1987).

"Adult Hemoglobin Synthesis by Reticulocytes from the Human Fetus at Midtrimester" by Morley D. Hellenberg, Michael M. Kaback, and Haig H. Kazazian, Jr., *Science*, vol. 174: 698–702, (1971).

"Hemoglobins in Human Fetuses: Evidence for Adult Hemoglobin Production After the 11th Gestational Week" by Haris A. Pataryas and George Stamatoyannopoulos, *Blood*, vol. 39: 688–696, (1972).

"Hemoglobin a Synthesis in the Developing Fetus" by Haig H. Kazazian, Jr. and Andrea P. Woodhead, *New England Journal of Medicine*, vol. 289: 58–62, (1973).

"Analysis of Peripheral Maternal Blood Samples for the Presence of Placenta–Derived Cells Using Y–Specific Probes and McAb H315" by A. Covone, et al., *Prenatal Diagnosis*, vol. 8: 591–607, (1988).

"Detection of Rare Cells at a Frequency of One Per Million by Flow Cytometry" by Hans–Joachim Gross, et al., *Cytometry*, vol. 14:519–526, (1993).

"Experimental test detects cancerous cells with record precision" *Arizona Daily Star*, Section A, p. 3, (1995).

"Model study detecting breast cancer cells in peripheral blood mononuclear cells at frequencies as low as $10^{-7}$" by Hans–Joachim Gross, et al., *Proc. Natl. Acad. Sci. USA*, vol. 92: 537–541, (1995).

"Isolation of fetal DNA from nucleated erythrocytes in maternal blood" by Diana W. Bianchi, et al., by *Proc. Natl. Acad. Sci.*, vol. 87: 3279–3283, (1990).

"Fetal cells in the blood of pregnant women: Detection and enrichment by fluorescence–activated cell sorting" by Leonard A. Herzenberg, et al., *Proc. Natl. Acad. Sci. USA*, vol. 76: 1453–1455, (1979).

"Detection and Isolation of Fetal Cells From Maternal Blood Using the Fluorescence–Activated Cell Sorter (FACS)" by G. Michael Iverson, et al., *Prenatal Diagnosis*, vol. 1: 61–73, (1981).

"First trimester prenatal diagnosis of trisomy 21 in fetal cells from maternal blood" by S. Elias, et al., *The Lancet*, vol. 340: 1033, (Oct. 24, 1992).

"Detection of fetal cells with 47,XY, +21 karyotype in maternal peripheral blood" by Diana W. Bianchi, et al., *Human Genetics*, vol. 90:368–370, (1992).

"Prenatal Diagnosis through the Analysis of Fetal Cell in the Maternal Circulation" by Diana W. Bianchi, M.D. and Katherine W. Klinger, Ph.D., *Genetic Disorders and the Fetus*, pp. 759–770, (1992).

"Identifications and Comparison of CD34–Positive Cells and Their Subpopulations From Normal Peripheral Blood and Bone Marrow Using Multicolor Flow Cytometry" by James G. Bender, et al., *Blood*, vol. 77: 2591–2596, (1991).

"Multiparameter flow–cytometrical quantitation of Circulating $CD34^+$–cells: correlation to the quantitation of circulating hemopoietic progenitor cells by in vitro colony–assay" by Stefan Serke, et al., *British Journal of Haematology*, vol. 77: 453–459, (1991).

"Detection of aneuploidy in human interphase spermatozoa by fluorescence in situ hybridization (FISH)" by R.H. Martin, et al., *Cytogenet Cell. Genet*, vol. 64: 23–26, (1993).

"Prenatal sex determination from maternal peripheral blood using the polymerase chain reaction" by Y.M. Dennis Lo, et al., *Human Genetics*, vol. 90: 483–488, (1993).

"Isolation of fetal trophoblast cells from peripheral blood of pregnant women" by U.W. Mueller, et al., *The Lancet*, vol. 336: 197–200, (1990).

"Fetal Lymphocytes in the Maternal Blood" by Jim Schröder and Albert de la Chapelle, *Blood, The Journal of Hematology*, vol. 39: 153–162, (1972).

"Fetal Leukocytes in the Maternal Circulation After Delivery" by Jim Schröder, Anja Thlikainen, and Albert de la Chapelle, *Transplantation*, vol. 17, No. 4: 346–354, (1974).

"Antenatal Sex Determination in Blood from Pregnant Women" by J.W. Siebers, et al., *Humangenetik*, vol. 28: 273–280, (1975).

"Elimination of Malignant Clonogenic Breast Cancer Cells from Human Bone Marrow" by Ian C. Anderson, et al., *Cancer Research*, vol. 49: 4659–4664, (1989).

"Prediction of Early Relapse in Patients with Operable Breast Cancer by Detection of Occult Bone Marrow Micrometastases" by Richard J. Cote, et al., *Journal of Clinical Oncology*, vol. 9, No. 10: 1749–1756, (1991).

"Further Studies on the Antenatal Detection of Sickle Cell Anemia and Other Hemoglobinopathies" by Haig H. Kazazian, et al., *Hemoglobin and Red Cell Structure and Function*, pp. 337–345, (1972).

"Detection of the Sickle Gene in the Human Fetus" by Yuet Wai Kan, et al., *The New England Journal of Medicine*, vol. 287: 1–5, (1972).

"Fluorescence In Situ Hybridization: A Sensitive Method for Trisomy 8 Detection in Bone Marrow Specimens" by Robert B. Jenkins, et al., *Blood*, vol. 79: 3307–3315, (1992).

"Cytogenetic Analysis in the Diagnosis of Acute Leukemia" by Sverre Heim, M.D., Ph.D. and Felix Mitelman, M.D., Ph.D., *Cancer*, vol. 70: 1701–1709, (1992).

METHOD FOR ENRICHMENT OF FETAL CELL POPULATION FROM MATERNAL WHOLE BLOOD SAMPLES

CROSS-REFERENCE TO RELATED APPLICATIONS

This application is a continuation-in-part of co-pending application Ser. No. 08/327,483 filed Oct. 21, 1994 which is commonly assigned.

BACKGROUND OF THE INVENTION

The present invention relates generally to separation of rare cell populations from whole blood samples. More particularly, the present invention provides a system and non-invasive method for enriching the populations of rare cells, such as nucleated fetal erythrocytes or nucleated fetal red blood cells ("NRBCs") obtained from maternal blood samples by separating the NRBCs from the mother's erythrocytes, leukocytes and other blood components. Those skilled in the art will appreciate that the present system and method are not confined, in their utility, to enrichment of fetal NRBCs. Rather, a wide variety of rare cell populations present in the peripheral blood circulation may be separated according to the present method, as will be explained more fully herein.

In accordance with a preferred embodiment thereof, the present invention offers a system and method for enriching a population of fetal-origin NRBCs from a maternal blood sample by a negative selection process which concentrates the NRBCs by lysis and yields viable rare cell populations which may be cultured or otherwise analyzed. While enrichment of viable fetal-origin NRBCs is described herein as an operative model of the present system and method, the present invention is not so limited in its utility.

Physicians have long sought to develop non-invasive methods for prenatal diagnosis because the available methods, amniocentesis and chorionic villus sampling (CVS) are potentially harmful to the mother and to the fetus. The rate of miscarriage for pregnant women undergoing amniocentesis is increased by 0.5–1%, and that figure is be slightly higher for CVS. Because of the inherent risks posed by amniocentesis and CVS, these procedures are offered primarily to older women, i.e., those over 35 years of age, who have a statistically greater probability of bearing children with congenital defects.

Some non-invasive methods have already been developed to diagnose specific congenital defects. For example, maternal serum alpha-fetoprotein, and levels of unconjugated estriol and human chorionic gonadotropin can be used to identify a proportion of fetuses with Downs syndrome, however, it is not one hundred percent accurate. Similarly, ultrasonography is used to determine congenital defects involving neural tube defects and limb abnormalities, but is useful only after fifteen weeks gestation.

The presence of fetal cells in the maternal peripheral circulation has been known for some time. However, fetal cells represent a rare cell population in maternal circulation present in estimated numbers ranging from 1 in 100,000 to 1 in 1,000,000. Fetal lymphocytes (Walknowska, et al., *Lancet* 1:1119 (1969), Schroder, et al., *Blood* 39:153 (1972; Schroder, *Scand J. Immunol.* 4:279 (1975)), syncytiotrophoblasts (Douglas et al., *Am. J. Obstet. Gynecol.* 78:960 (1959); Goodfells, et al., *Brit. J. Obstet. Gynecol.* 89:65 (1982); Covone, et al., *Lancet* 2:841 (984); Kozma, et al., *Hum. Reprod.* 1:335 (1986)), cytotrophoblasts (Mueller, et al., *Lancet* 336:197 (1990)), and erythrocytes (Freese, et al., *Obstet. Gynecol.*, 22527 (1963); Clayton, et al., *Obstet. Gynecol.* 23:915 (1964); Schroder, *J. Med. Genet.* 12:230 (1975; Medaris, et al., *Am. J. Obstet. Gynecol.* 148:290 (1984)) have been identified in the maternal peripheral blood circulation.

Separation of nucleated fetal erythrocytes from maternal blood has been identified as a desirable method for facilitating prenatal diagnosis of genetic disorders. Fetal NRBCs have been separated from maternal blood by flow cytometry using a lysing reagent (European Published Patent Application No. 582736, published Feb. 16, 1994); by triple gradient discontinuous gradient gel electrophoresis (Bhat, et al, U.S. Pat. No. 5,275,933, issued Jan. 4, 1994); by separation from nucleated cells using leukocyte depletion and ammonium chloride lysis of enucleated erythrocytes (Goldbard, PCT Publication WO 9417209, published Aug. 4, 1994); by use of anti-CD71 monoclonal antibody and magnetic beads and in-situ fluorescence hybridization (FISH) (Ahlert, et al, German Published Patent Application No. 4222573, published Aug. 12, 1993) or by other antibodies specific to a fetal erythrocyte antigen (Bianchi, PCT Publication WO 9107660, published May 30, 1991). Unfortunately, to date, there are no clinically acceptable methods for prenatal genetic diagnosis using maternal peripheral blood samples. Amniocentesis and CVS continue to be the only options available to a small percentage of pregnant women. These women represent the group statistically at risk of conceiving a fetus having genetic abnormalities.

Substantial attention has been given to methods of prenatal sex diagnosis using fetal cells in the maternal peripheral blood. Because obtaining a maternal blood sample is far less invasive than amniocentesis, CVS or fetal blood sampling, methods which capable of enriching fetal cells from maternal peripheral blood samples have become a paramount focus of neonatology. Many studies have been made on prenatal sex diagnosis by means of the polymerase chain reaction (PCR) amplifying the Y-chromosome-specific DNA sequence in maternal blood. See, e.g., Bianchi, D. W., et al., *Proc. Natl. Acad. Sci. USA*, 87:3279–3283 (1990), Bianchi, D. W., et al. *Prenat. Diagn.*, 13:293–300 (1993), Wachtel, S., et al., *Hum. Reprod.*, 6:1466–1469 (1991), Suzemori, K., et al., *Obstet. Gynecol.*, 80:150–154 (1992). In some of the studies using PCR amplification, fetal cells in the maternal blood were enriched and analyzed by PCR. While the sensitivities and specificities of the methods reported in the PCR studies is high, e.g., 64–100 and 80–100 percent, respectively, and the positive and negative predictive values were 75–100 and 67–100 percent, respectively, the diagnostic accuracy reported in each study was insufficient to be acceptable for routine clinical use. Hamada, H., et al., *Prenat. Diag.*, 15:78–81 (1995).

Flow cytometry has also been used to separate fetal NRBCs on the basis of positive CD71 antibody (transferrin receptor) and glycophorin-A antibody binding. PCR conducted on the flow-sorted cells identified male fetuses at a rate of 100% accuracy and female fetuses at a rate of 83% accuracy. Simpson, J. L., et al., *J. Am. Med. Ass'n.* 270:2357–2361 (1993). Immunogenetic procedures have been combined with fluorescence-activated cell sorting (FACS) procedures to enrich fetal cells in whole blood from pregnant women. Herzenberg, L. A., et al., *Proc. Natl. Acad. Sci. USA*, 76:1453–1455 (1979) employed rabbit anti-HLA-A2 antibodies in conjunction with fluorescein-conjugated goat anti-rabbit immunoglobulins and analyzed the fluorescein-bound cells using FACS.

Fluorescence in situ hybridization (FISH) offers a method for identifying desired DNA in a cell at the interphase stage.

FISH with conventional cytogenetic methods has been used on fetal cells recovered from maternal blood samples for sex determination, Wessman, M., et al., *Prenat. Diag.*, 12:993–1000 (1992), and to detect chromosomal abnormalities, Simpson, J. L., et al., *Prenat. Diag.*, 12:S12 (Supp. 1992) [fetal trisomy 21], Bianchi, D., et al, Prenatal Diagnosis through the Analysis of Fetal Cells in the Maternal Circulation, *Genetic Disorders and the Fetus* 3d Ed., Milunsky, A., ed., pp. 759–770 (1992) [Fetal trisomy 18].

Fetal progenitor cells have also been enriched from maternal blood by ligand binding onto an immobilization medium. CellPro, Inc., International Publication No. WO 94/25873, published Nov. 10, 1994, discloses an immunoselection method for enriching fetal erythroid progenitor cells from maternal blood by separating a large fraction of maternal erythrocytes from the blood sample, such as by density gradient centrifugation on a Ficoll gradient or by preferential lysis of maternal erythrocytes in the presence of ammonium chloride, potassium chloride and a carbonic anhydrase inhibitor, then incubating a sample of maternal blood with a ligand to bind fetal progenitor cells and then removing unbound blood products, leaving the enriched, ligand-bound fetal erythroid progenitor cells. The ligands disclosed include antibodies, erythropoietin or transferrin. The ligand is immobilized on any of a variety of solid supports, such as hollow fibers, magnetic beads, plates, dishes, flasks, meshes, screens, solid fibers, membranes or dipsticks.

The CellPro International Publication, discloses, for example, the use of first member-second member binding pairs, including biotin-avidin, biotin-streptavidin, biocytin-avidin, biocytin-streptavidin, methotrexate-dihydrofolate reductase, 5-fluorouracil-thymidylate synthetase and riboflavin-riboflavin binding protein, wherein the first binding member is linked to a ligand capable of binding fetal nucleated erythroid cells, the second binding member is linked to an immobilization medium, and the second member has a binding affinity constant for the second member of greater than about $10^8$ $M^{-1}$. The preferred embodiments disclosed include methods for positive and negative selection of fetal cells, useful independently or in conjunction with one another. The positive selection process using a binding pair consisting of biotinylated anti-CD34 antibody and immobilized avidin. The CD34 antigen is expressed on fetal progenitor cells and hematopoietic progenitor cells, however, in normal adults, the hematopoietic progenitor cells reside in the bone marrow and CD34 positive cells are found in the peripheral circulation at a rate of less than 0.1%. The negative selection process using a binding pair consisting of biotinylated anti-CD45 and immobilized avidin. The CD45 antigen is expressed on maternal erythrocytes, but not fetal progenitor cells. The immunoselected fetal cells then may be subjected to analysis by karyotyping, PCR, RFLP, SSCP or FISH to provide genetic or biochemical information. The CellPro method, however, suffers from a clinically unacceptable yield of enriched cells. While this published application states enrichment of fetal progenitor cells to a concentration greater than 1%, the highest level of enrichment supported by the examples was attained by a dual positive selection process using sequential CD34 antibody binding steps yielding a sample containing about 1 in 2,000 or 0.5% fetal cells, representing about a 500-fold enrichment from the starting sample.

To date, however, no clinically acceptable method for enrichment of rare cell populations, particularly fetal nucleated erythrocytes, from peripheral blood samples has been devised which yields cell populations sufficient to permit clinical diagnosis. The clinical need for a method capable of producing higher yields of rare fetal cell populations separated from maternal whole blood was recently underscored by Hamada, H., et al., *Prenat. Diag.* 15:78–81 (1995) who stated that "The data obtained in this study suggest that fetal sex determination using maternal peripheral blood with FISH is possible and that this diagnostic method will be clinically useful when more cells are analyzed."

SUMMARY OF THE INVENTION

The present invention provides a system and method for separation of viable, culturable fetal nucleated red blood cells from maternal whole blood constituents at clinically useful levels. The enriched fetal NRBCs are present in numbers sufficiently large for effective cell culture and subsequent genetic diagnosis with conventional and cytogenetic methods, as well as emerging DNA methods such as PCR, RFLP, SSCP, FISH chromosome banding and karyotyping.

The present invention achieves its objectives by a) density gradient centrifugation of whole blood to provide a gross separation of a major fraction of maternal erythrocytes and blood plasma from whole blood, b) charged-flow separation of the gross separated whole blood to separate fetal erythroid progenitor cells from maternal myeloid and lymphold cells, c) ammonium lysis of remaining maternal erythrocytes and d) complement mediated lysis to remove myeloid and lymphold cells present in the charged flow separated fractions. The inventive system and method achieves enrichment of rare cell populations, fetal erythroid progenitor cells, specifically, CFU-GEMM (colony forming unit, granulocyte, erythroid, megakaryocyte, monocyte), BFU-E (burst-forming unit, erythroid), CFU-E (colony-forming unit, erythroid), pronormoblasts, normoblasts (erythoblasts), and reticulocytes by negative selection for the desired cell population.

The charged-flow separation (CFS) apparatus described in the co-pending application Ser. No.: 08/327,483 filed Oct. 21, 1994 (hereinafter "Twitty, et al."), which is hereby incorporated by reference, or as described in our U.S. Pat. Nos. 5,336,387 and 5,173,164, which are also hereby incorporated by reference, is ideally suited for separation rare cell populations from whole blood. The CFS apparatus is preferably run under sterile conditions to yield culturable separated cells. Under charge-flow separation conditions, as described in the Twitty, et al application, or as described in U.S. Pat. Nos. 5,336,387 or 5,173,164, incorporated by reference, fetal erythroid progenitor cells exhibit consistent migration patterns in an electric field according to surface charge density which are different and distinct from the migration patterns of mature enucleated erythrocytes. By using the CFS apparatus coupled with the pre- and post-processing methods described more fully hereinafter, the present invention has achieved enrichment of up to 12 percent of rare cell populations in the final sample.

The CFS system and method has been successfully used to recover nucleated red blood cells from the peripheral blood circulation of pregnant women. The recovered NRBCs were identified histologically. The NRBCs exhibited consistent migration patterns whether they came from maternal blood or from umbilical cord blood collected at birth. No NRBCs were found in blood from nulliparous women.

Because the inventive system and method of charge-flow separation of NRBCs from maternal blood is based on the intrinsic physical properties of the NRBCs, there is little need for extensive preparation of the maternal blood sample with antibodies or ligands. The cells may be processed at greater than or equal to 60,000 cells per second and specialized training is not required. When the inventive charge-flow separation system and method is used, the recovered cells are viable, thus raising the possibility of further enrichment by cell culture.

In conjunction with or in addition to the charge-flow separation system and method, the present invention also includes an affinity separation method for separating NRBCs from other cell populations in a maternal blood sample. The adsorption-filtration affinity method of the present invention entails layering a maternal blood sample onto a fibrous adsorption-filtration filter medium having a nominal pore size of about 8 microns and being capable of 40–80% leukocyte immobilization, with a 70–80% post-wash leukocyte retention rate, and which is extremely hydrophilic, being capable of wetting with solutions having surface tensions of up to 85–90 dynes, which has a hold up volume of 40–70 $\mu l/cm^2$ for a single layer of adsorption-filtration filter medium and which is characterized by low to medium protein binding. The preferred adsorption-filtration separation filter medium is that sold by Pall Corporation under the trademarks "LEUKOSORB" TYPES A and B or that described in U.S. Pat. Nos. 4,923,620, 4,925,572, or European Patent No. 313348, each of which is hereby incorporated by reference.

The charge-flow separation system and method and the adsorption-filtration separation system and method of the present invention may be used separately or may be used in conjunction with one another to achieve enrichment of the nucleated fetal red blood cell population in a maternal blood sample.

DESCRIPTION OF PREFERRED EMBODIMENTS

Figure 1:
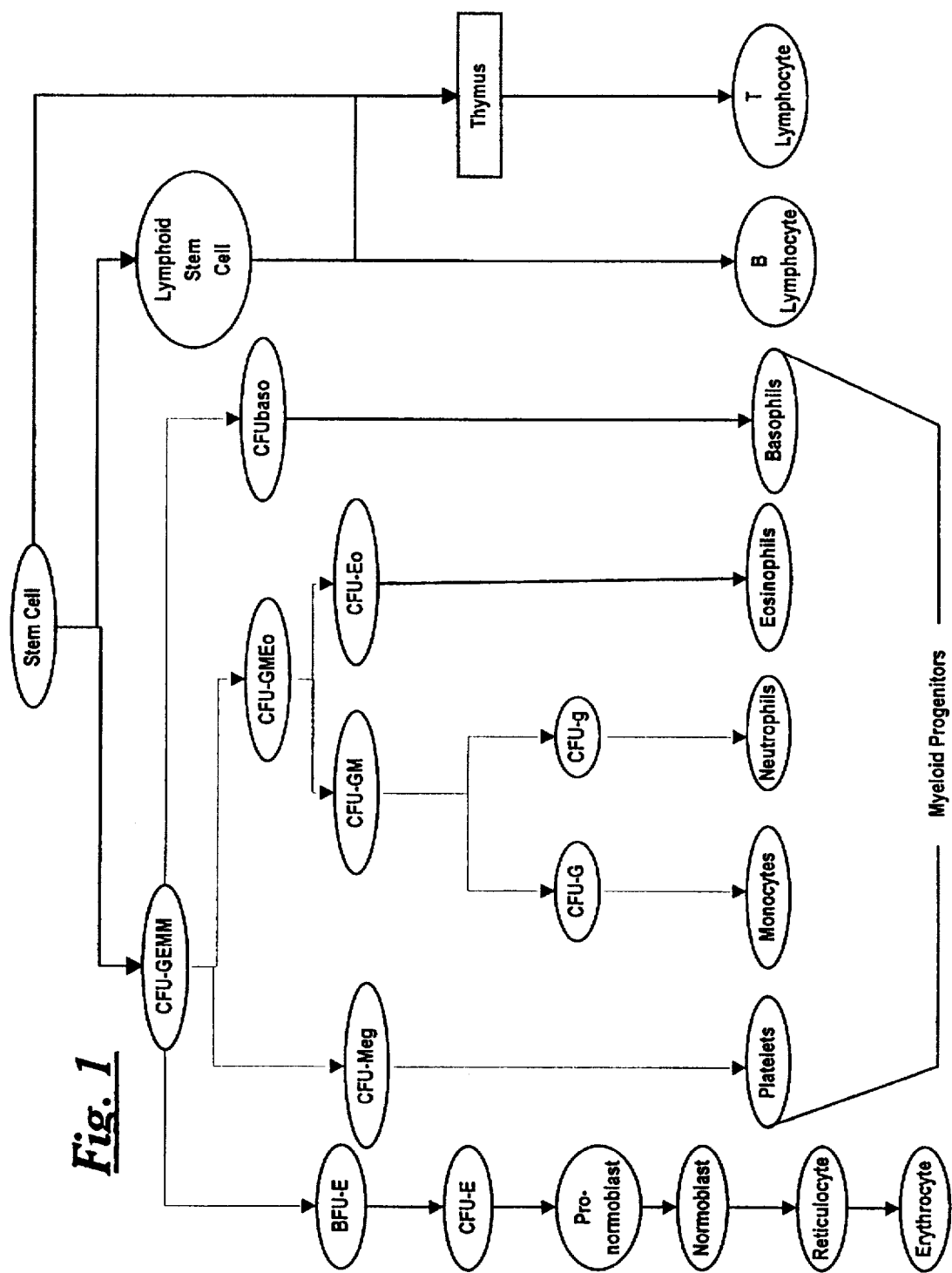
FIG. 1 is a flow diagram of representing hemopoiesis and differentiation between erythroid, myeloid and lymphoid cell lines.

FIG. 1 is a diagram depicting the hematopoietic system and progenitor hierarchy starting from a common pool of pluripotent hematopoietic stem cells, through commitment to erythroid, myeloid and lymphoid cell lines, to unique morphology cell lines. As those skilled in the art will understand, the process of mature blood cell production from stem cells is a complex series of irreversible cellular differentiation and amplifying proliferation events. The hematopoietic system provides the backdrop against which the system and method for separating rare cell populations from whole blood may be viewed.

It is well known in the art that as stem cells differentiate during hematopoiesis, the maturing cells undergo morphological changes. Concomitant with these morphological changes, the cells develop different sets of surface molecules, i.e., proteins, polysaccharides, etc., such as those exemplified by the cluster differentiation (CD) series to classify the surface molecules. Antibodies specific for different surface molecules, such as the CD series, may then be used to identify the presence of specific cell populations in a blood sample. It has been found, however, that various erythroid, myeloid and lymphoid cells share some common CD surface molecules, as do individual cell types within each development family, e.g., erythropoietic cells. These shared CD surface molecules make selection processes cumbersome. A good summary of principal features of known CD molecules present in hematopoietic cell lines is found in Hoffbrand, A. V., et al., *Essential Haematology*, 3d ed., Blackwell Scientific Publications, pp. 417–418, (1993), hereby specifically incorporated by reference thereto.

Figure 2:
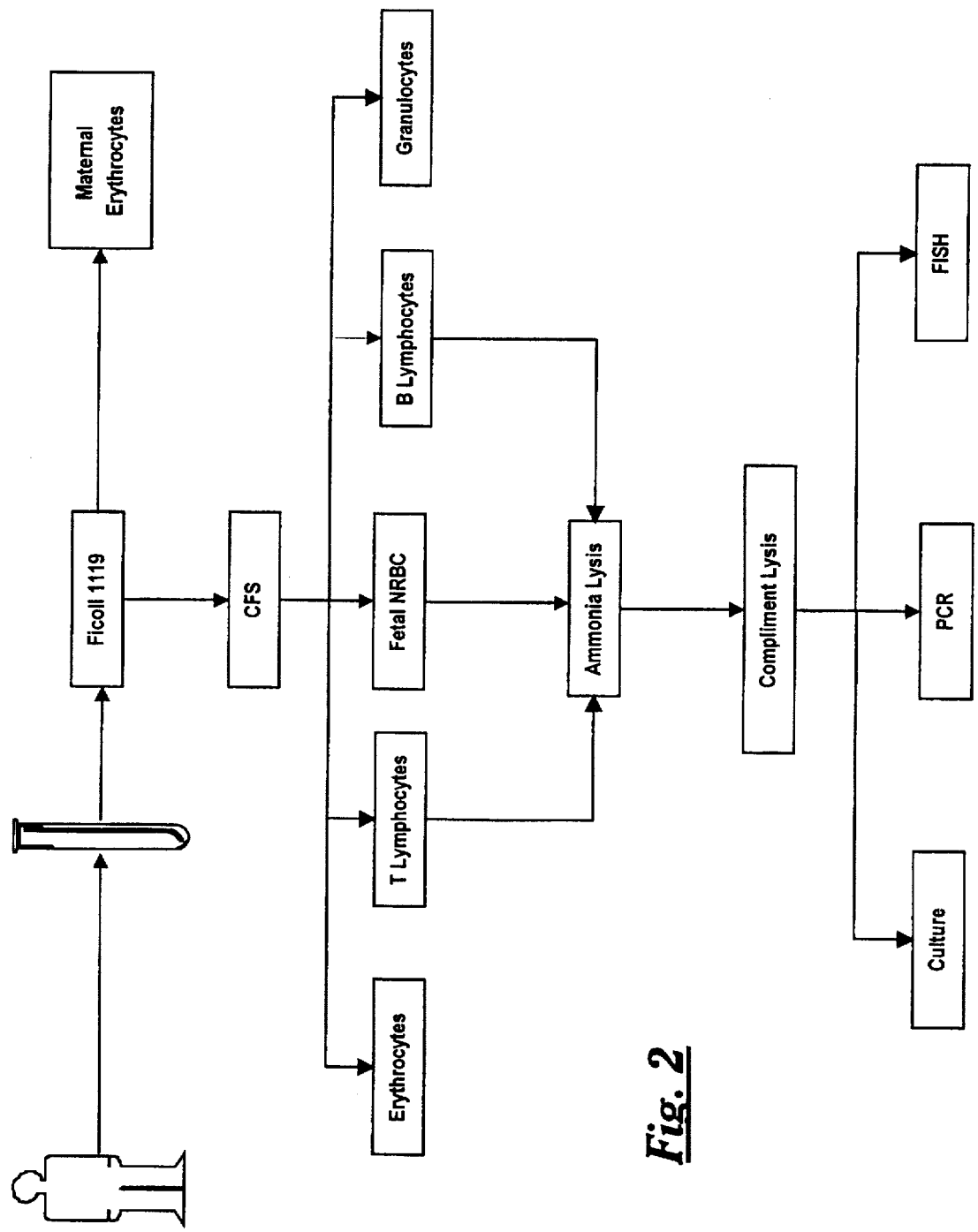
FIG. 2 is a flow diagram of the inventive enrichment process for separating rare cell populations from whole blood.
Figure 3:
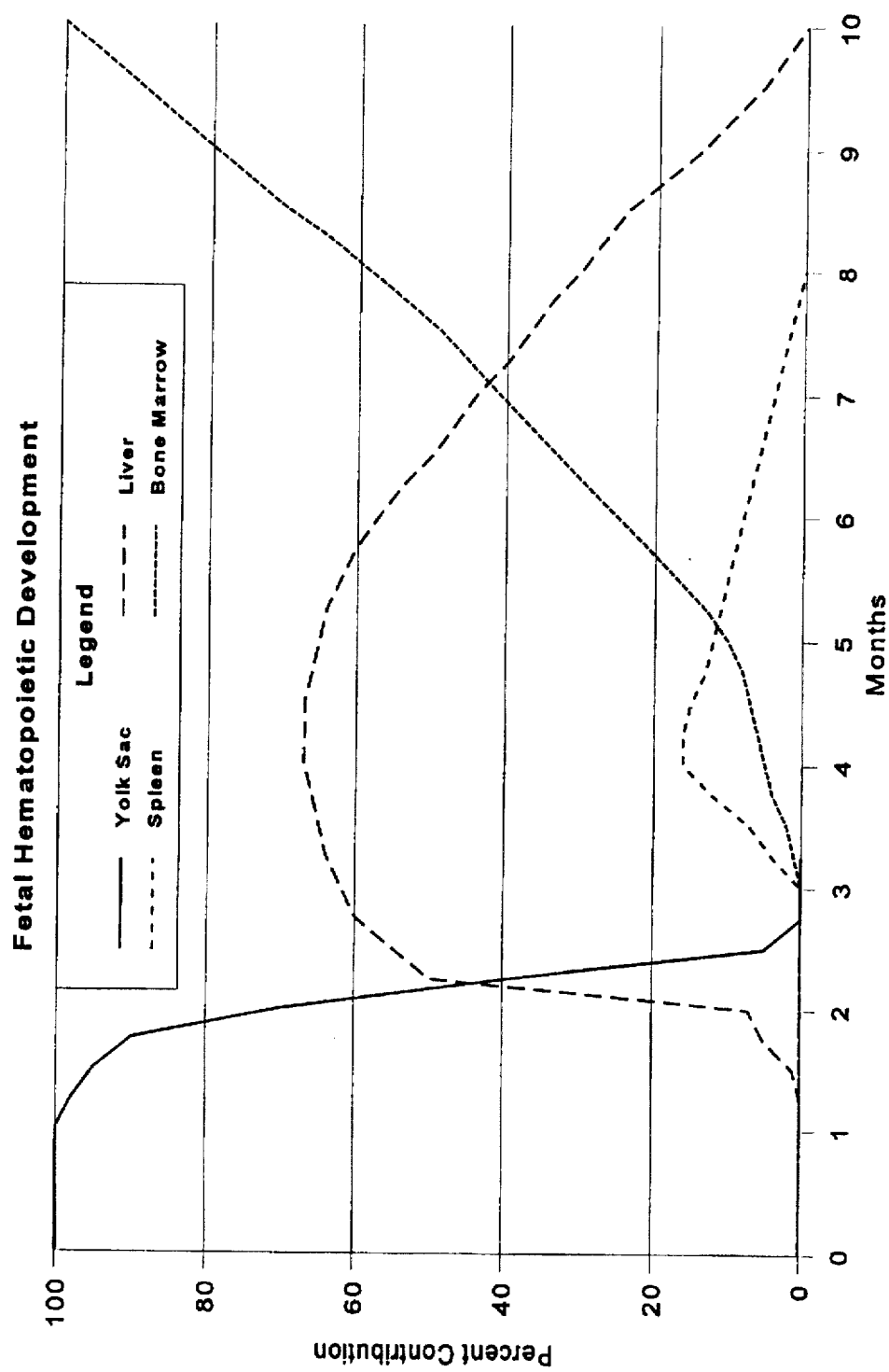
FIG. 3 is a graph representing fetal hematopoietic development and sites during gestation.

In accordance with a first preferred embodiment of the present invention, and with particular reference to FIG. 2, there is provided a method for enriching rare cell populations from whole blood. It is axiomatic that all healthy human blood samples, whether male, female, child or adult, young or aged, irrespective of blood type and Rh factor, is constituted of a full range of blood cell types along the hematopoietic hierarchy depicted in FIG. 1. When a person is afflicted with a particular cellular disorder, such as breast cancer, prostate cancer, lung cancer, leukemia, or the like, abnormal cells representative of the disorder are usually found, in varying degrees, as rare populations in the peripheral blood circulation. Similarly, it is well known that fetal-origin cells may be found at very low levels, i.e., $1 \times 10^{-6}$ to $1 \times 10^{-7}$, in the maternal peripheral blood circulation. By using alternating negative selection steps (defined herein as selecting the undesired cell populations by any means, including antibody or ligand binding, filtration, or manual selection) and positive selection steps (defined herein as selecting the desired cell populations, including antibody or ligand binding, filtration, or manual selection), the system and method of the present invention isolates rare cells from peripheral blood, by enriching the desired rare cell population from whole blood.

As depicted in FIG. 2, a peripheral blood sample 12 is obtained from a subject 10, by any conventional technique known in the art, such as by venipuncture, usually of the antecubital vein. The volume of blood collected typically ranges between 20–40 ml, but may be more or less. The blood is collected in vacuum containers, typically in the presence of one or more anticoagulants, as desired, including acid-citrate-dextrose (ACD), ethylenediaminetetraacetic acid (EDTA), heparin, and citrate-phosphate-dextrose-adenine (CPDA). The collected blood sample may be stored for up to 4 days at 4° C. It is preferable, however, to process and analyze the blood sample within 24 hours of collection. It has been found that after 24 hours, the blood sample will undergo changes, such as maturation of some hematopoietic cells present in the blood sample.

The whole blood sample is layered onto Ficoll/Hypaque-1119 (polysucrose type 400/sodium diatrizoate, 1.119 g/ml)

(HISTOPAQUE-1119, Sigma Chemical Company) density gradient and centrifuged at about 400×G for about 40 minutes. After centrifugation, plasma forms a top layer, a white band of nucleated cells, including nucleated erythroid cells and lymphocytes, is immediately below the plasma layer, the Ficoll/Hypaque-1119 containing a broad diffuse band containing other nucleated erythroid cells and immature red cells with densities heavier than the white layer but lighter than the mature erythrocyte pellet is immediately below the nucleated cells and the erythrocyte pellet is present at the very bottom of the tube.

The plasma fraction is discarded and the nuclear fraction is removed by decanting or aspiration without disturbing the nuclear fraction. The nucleated cell portion is removed to a separate sterile centrifuge tube, washed in phosphate buffered saline and prepared for loading onto the charged flow separator apparatus 20 and subjected to charged flow separation as more fully disclosed in the Twitty, et al. patent application and U.S. Pat. Nos. 5,336,387 and 5,173,164, incorporated by reference, under conditions to maintain a sterile environment.

It has been found that the mobility of fetal NRBCs in an electric field is intermediate between the fastest enucleated red blood cells and the slowest white blood cells. Thus, for example, where enucleated red blood cells 22 elute in fractions 4–7, and leukocytes elute from fractions 6–8, it has been found that the nucleated fetal red blood cells elute in fractions 5–8 with the peak in fraction 7. Based upon these findings, it has been determined that fetal NRBCs 26 have electrophoretic mobilities more similar to many mononuclear cells of lymphoid origin 24, such as T lymphocytes and B lymphocytes, than to erythrocytes 22 or a majority of granulocytes 29 or other cells of myeloid origin. It is desirable, therefore, to collect not only the peak fraction, but also the two fractions adjacent the peak fraction, e.g., fractions 6 and 8. In this manner, the nuclear fraction eluting from the CFS apparatus is separated from a major fraction of mature erythrocytes, granulocytes and other cells of myeloid origin in the original blood sample.

To test the suitability of CFS-separation as a clinically acceptable separation tool for providing cells for clinical diagnosis, sex determination, fluorescence in situ hybridization (FISH) was performed on the CFS-separated nucleated cell portion. FISH analysis confirmed that the CFS enrichment method, as described above, obtains enrichment levels sufficient to make clinically reliable diagnoses. Ficoll/Hypaque-1119 density gradient centrifugation, followed only by CFS-separation, yielded fetal NRBC frequencies in the range of 1/20 to 1/50, or about 2–5% fetal NRBCs. Table 1, below, summarizes data from blood samples obtained from five pregnant women at 20-30 weeks gestation, together with blood samples from a nulliparous female control and a male control. All samples were processed as described above and analyzed by FISH using a DYZ1/DYZ3 probe specific for the Y chromosome.

TABLE 1

| Case | Gestation (Weeks) | Fetal Sex | Nuclei Labeled/ Nuclei Counted | Percent Labeled |
|---|---|---|---|---|
| 1 | NR | Male | 15/1000 | 1.5 |
| 2 | 20.5 | Male | 15/1000 | 1.5 |
| 3 | 30 | Male | 46/2500 | 1.8 |
| 4 | 20 | Male | 13/1000 | 1.3 |
| 5 | 23 | Male | 29/1000 | 2.9 |

TABLE 1-continued

| Case | Gestation (Weeks) | Fetal Sex | Nuclei Labeled/ Nuclei Counted | Percent Labeled |
|---|---|---|---|---|
| Male Control | | | 988/1000 | 98.8 |
| Female Control | | | 3/1000 | 0.3 |

Figure 4:
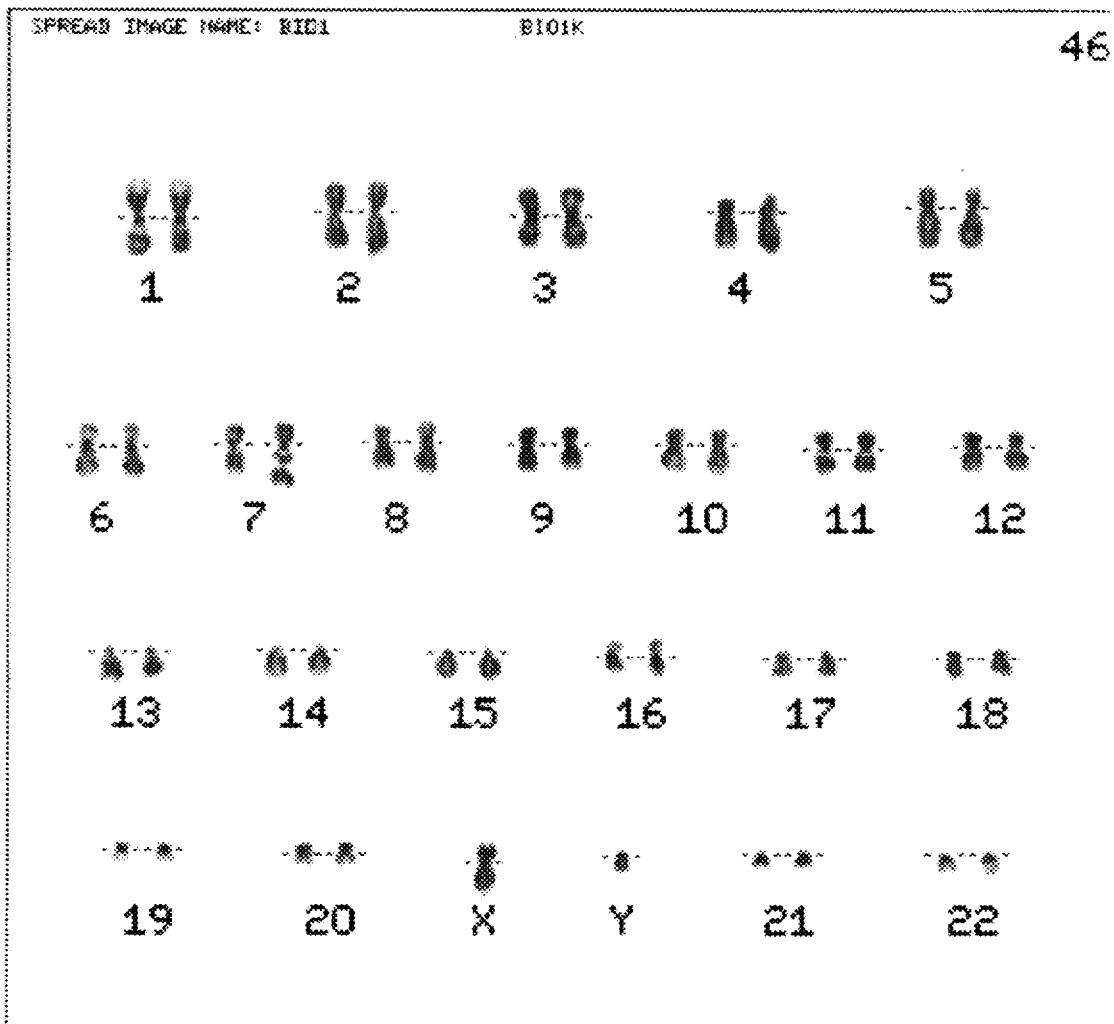
FIG. 4 is a karyotype image of a 51 year old male obtained from cultured erythroid progenitor cells isolated from a whole blood sample using the method of the present invention.

The suitability of the CFS-enriched fetal NRBCs for clinical prenatal genetic diagnosis was determined by processing whole blood samples from one woman taken two days post-partum with a stillborn delivery and two pregnant women who had previously undergone amniocentesis at 16 and 19 weeks, respectively, with known results. Karyotyping of the still-born fetal blood sample confirmed a positive fetal trisomy 18 with karyotype 47,XX,+18, while amniocentesis on second subject indicated a fetal karyotype 47,XX,+21 and third subject indicated a fetal karyotype 47,XY,+21+m, both confirming positive fetal trisomy 21. Blood samples from normal adult males were used as controls. An example of a karyotype from a normal adult male is presented as FIG. 4.

The subjects' blood samples and the controls were processed by Ficoll-1119 gradient centrifugation followed by CFS-separation as described above. Following charged flow separation, the trisomy 18 positive sample and the first male control sample were analyzed by FISH using a chromosome-21-specific probe, and the trisomy 21 positive samples and the second male control sample were analyzed using a chromosome-21-specific probe. The data for the known fetal trisomy 18 sample is presented below in Table 2 and the data for the known fetal trisomy 21 sample is presented below in Table 3.

TABLE 2

| Sample | Percent nuclei containing n signals | | | | |
|---|---|---|---|---|---|
| | n = 0 | 1 | 2 | 3 | ≧4 |
| Trisomy 18 | 3 | 26 | 70 | 2 | 0 |
| Control A | 0 | 5 | 95 | 0 | 0 |
| Control B | 0 | 21 | 79 | 0 | 0 |

TABLE 3

| Sample | No. Cells Scored | Percent nuclei containing n signals | | | | |
|---|---|---|---|---|---|---|
| | | n = 0 | 1 | 2 | 3 | ≧4 |
| Case 1 | 1000 | 6 | 16 | 69 | 7 | 2 |
| Case 2 | | | | | | |
| Sample 2 (a) | 1000 | 11 | 23 | 61 | 5 | 0.4 |
| Sample 2 (b) | 200 | 0 | 1 | 93 | 4 | 2 |
| Sample 2 (c) | 500 | 26 | 36 | 36 | 2 | 0 |
| Control | 500 | 3 | 24 | 73 | 0.4 | 0 |

Table 4, below, summarizes the results of genetic detection of CFS-processed fetal cells analyzed by FISH in accordance with the FISH protocol published and distributed by Oncor, Inc. as of the date of this application for use with the Oncor, Inc. FISH kit, which is hereby incorporated by reference.

TABLE 4

| Probe | No. Samples | Sample Type | Mean % Cells Labeled (SD) |
|---|---|---|---|
| DYZ1/DYZ3 | 5 | Experimental | 1.8 (0.6) |
| (Y Chromosome) | 2 | Male Control | 98.8 (0.8) |
|  | 2 | Female Control | 0.3 |
| D18Z1 | 1 | Experimental | 2.0 |
| (Chromosome 18) | 2 | Male Control | 0 |
| D21S1219/ | 2 | Experimental | 5.3 (2.4) |
| D21S1220 | 1 | Female Control | 0.4 |
| (Chromosome 21) |  |  |  |

Because the relative mobilities of lymphocytes and fetal NRBCs are similar, it was deemed desirable to further enrich the fetal NRBC population obtained by charge flow separation. The charge flow separated sample was then further enriched by negative selection of the remaining erythrocytes and myeloid cell populations.

The enriched nucleated cell fraction eluting from the CFS apparatus typically contains a small fraction of mature erythrocytes, a major fraction of mononuclear lymphoid cells, such as B and T lymphocytes, a minor fraction of fetal NRBCs and a minor fraction of myeloid-lineage cells.

Ammonia hemolysis 30 preferentially eliminates mature erythrocytes from the enriched nucleated CFS fetal cell eluate. The rate controlling factor in ammonium hemolysis is the level of erythrocytic carbonic anhydrase present in the cell. Fetal erythroid cells have carbonic anhydrase levels one-fifth those of adult erythroid cells. As a result of this difference in carbonic anhydrase levels, selective ammonium hemolysis of mature erythroid cells is controlled as a time-rate function, i.e., for any given time period, adult red cells will lyse five times faster than fetal cells.

The enriched nuclear CFS eluate is incubated in the presence of ammonia or ammonia salts, for example ammonia chloride, chloride ions, for example sodium chloride, potassium chloride, magnesium chloride or calcium chloride, and a carbonic anhydrase inhibitor, such as acetazolamide, cyanide, cyanate, monovalent sulfides or sulfonamides, under conditions and for a time sufficient to allow ammonium ion transport within the cells, as described in Jacobs and Stewart, *J. Gen. Physiol.* 25:539–552 (1942), or Maren and Wiley, *Molec. Pharmacol.* 6:430–440 (1970), followed by incubation in the presence of ammonia and carbon dioxide, to preferentially lyse adult erythrocytes in the sample.

The lysed erythrocytes are separated by centrifugation and the pellet is resuspended in PBS. The resulting product is now substantially free of maternal erythrocytes, but contains fetal nucleated erythroid cells and maternal myeloid and lymphoid cells. To remove a substantial number of maternal myeloid and lymphoid cells remaining in the sample, compliment lysis 32 of the myeloid and lymphoid cells is undertaken. For example, anti-human CD37 IgM is added to the PBS suspension and allowed to bind to human lymphocytes present in the sample. After binding, rabbit complement is added and the resulting samples are allowed to incubate. Following incubation, incomplete Iscove's medium with only fetal calf serum (FCS) is added to the sample and the sample is centrifuged. The resulting pellets are may be prepared for culture 34, PCR 36, FISH 38 or other analytical method as desired in accordance with analytical protocols well known in the art. It is desirable to resuspend the pellet in Iscove's medium with only FCS and remove and treat aliquots using 3% acetic acid and crystal violet to lyse erythrocytes and stain nuclei. Nucleated cell counts of the aliquots may then be made under light microscopy.

In accordance with a further preferred embodiment of the invention, the resuspended cells are prepared for cell culture by diluting the cells with incomplete Iscove's medium in the presence of FCS so that each 0.1 mL contains $4 \times 10^5$ nucleated cells. 0.1 mL of incomplete Iscove's medium containing $4 \times 10^5$ nucleated cells is then added to 1.0 mL of complete Iscove's medium (containing growth factors and methylcellulose), which is then added to a 35 mm Petri dish and cultured according to standard culture protocols as described in *Colony Assays of Hematopoietic Cells Using Methylcellulose Media. An Introductory Technical Manual*, Terry Fox Laboratory Media Preparation Service, Vancouver, B.C., Canada, 1992 ed., hereby incorporated by reference.

The plates are scored for colonies at day 10–12 and again at day 18–21. At day 10–12, CFU-E and mature BFU-E colonies are noticeable, and at day 18–21, primitive BFU-E, CFU-GM and CFU-GEMM colonies are present and may be scored. At any desired point in colony growth, so long as mitotic cells are present, growth is synchronized via 5-fluorouracil block and thymidine release of the 5-fluorouracil block. See, e.g., Fraser, et al., *Cancer Genetics, Cytogenetics*, 24:1–6 (1987), hereby incorporated by reference for the 5-fluorouracil block procedures. Cellular growth is subsequently arrested in the metaphase portion of mitosis, using colecemid colcemid, colchicine, or similar substance, so that high mitotic indices may be obtained and karyotypes prepared. Growth synchronization is an optional, but preferred stem and usually yields higher mitotic indices.

EXAMPLE 40 mL of whole blood was collected from a pregnant female by venipuncture. The blood sample was anticoagulated with CPD (2.55 g d-glucose, 2.63 g sodium citrate, 0.327 g citric acid and 0.222 monobasic sodium phosphate in 100 mL distilled water) and placed in a 50 mL sterile centrifuge tube. A 50–100 ul aliquot was removed to take erythrocyte and lymphocyte counts. HISTOPAQUE-1119 (Ficoll/Hypaque-1119, polysucrose type 400/sodium diatriazote, 1.119 g/ml, Sigma Chemical Company, Catalog Number 1119-1) was warmed to 37° C. in a water bath. The blood may be held at room temperature or in the water bath at 37° C.

20 mL of HISTOPAQUE-1119 was aseptically placed into each of two sterile 50 mL centrifuge tubes and 20 mL of blood is carefully layered on top of the HISTOPAQUE-1119 in each tube. If there is an insufficient blood volume available to yield two 20 mL fractions, sterile phosphate buffered saline may be used to bring the blood volume in each tube to 20 mL. The blood-HISTOPAQUE layered tubes are centrifuged at 430×G in a Sorvall HS-4 swing bucket rotor for 40 minutes at room temperature. After centrifugation, the upper plasma layer in each tube was decanted then discarded. The white nucleated cell band immediately above the HISTOPAQUE-1119 along with the diffuse erythroid band in the HISTOPAQUE-1119 were removed with a pipette and combined in a separate sterile 50 mL centrifuge tube. The mature erythrocyte pellet was discarded.

Sterile PBS at 37° C. was added to the nuclear fraction pipetted to a separate sterile 50 mL centrifuge tube to a volume of 50 mL, and centrifuged at 1750 RPM for 20 minutes. The supernatant was decanted and the resulting pellet resuspended in 50 mL sterile PBS and centrifuged at 1500 RPM for 20 minutes. The supernatant was decanted and the pellet resuspended in 5 mL of buffer (triethanolamine, 5 mM; glycine, 280 mM; glucose, 22 mM, acetic acid to pH 7.3). The re-suspended cells were processed the a CFS apparatus configured with 12 separation channels, 10 counterflow input channels and 4 counterflow output channels. 5 mL of the cells resuspended in buffer were introduced in a sample input flow, with the sample buffer input having a flow rate of 0.220 ml/min/channel, with a buffer output flow rate of 0.370 ml/min/channel and a counterflow pump rate of 4.0 ml/min, in the presence of an applied electric field of 325 V at 50–55 mA.

After the CFS run, 12 fractions were collected in 50 mL centrifuge tubes. Fractions 4–6 were determined to contain cells and the fractions collected in centrifuge tubes 4–6 were centrifuged at 1750 RPM for 20 minutes, the supernatant was decanted and the resulting pellet was resuspended in 5–10 mL of sterile PBS and recentrifuged at 1500 RPM for 10 minutes.

The supernatant was decanted and 10 mL of ammonium lysate (1 mL $10^{-3}$ acetazolamide, 9 mL NaCl and 90 mL of 0.1844 $NH_4Cl$) was added to each tube and incubated at room temperature for 3 minutes. After incubation, 2 mL of a 3 mM solution of $NH_4HCO_3$ was added to each tube and incubated for an additional 4 minutes at room temperature. The tubes were then centrifuged at 1500 RPM for 10 minutes and the supernatant decanted. The pellets were resuspended in 0.9 mL of sterile PBS and 1 ug of anti-human CD37 IgM (Research Diagnostics) was added to each tube and each tube was agitated until antibody was completely disbursed. After the antibody is dispersed, 100 ul of Low Tox Rabbit Complement for human lymphocytes (Accurate Antibody, Cedar Lane Laboratories, Hornby, Ontario, Canada) was added to each tube and incubated at 37° C. for 30 minutes.

Following incubation with antibody and complement, 12 mL of incomplete Iscove's medium with 2% FCS (Stem Cell Technologies, Vancouver, B.C., Canada) was added to each tube and the tubes centrifuged at 1500 RPM for 10 minutes. The supernatant was removed and the pellets were resuspended in 0.5–5 mL of incomplete Iscove's medium with 2% FCS. Aliquots were removed and fixed with 3% acetic acid and crystal violet to lyse erythrocytes and stain nuclei. Nucleated cell counts were made on each aliquot.

The resuspended cells were then re-diluted with incomplete Iscove's medium with 2% FCS to a concentration of $4 \times 10^5$ nucleated cells per 0.1 mL. 0.1 mL of re-diluted cells was added to 1.0 mL of complete Iscove's medium, containing growth factors and methyl cellulose), and this amount, 1.1 mL, was added to a 35 mm Petri dish and placed into culture in accordance with *Colony Assays of Hematopoietic Cells Using Methylcellulose Media. An Introductory Technical Manual*, Terry Fox Laboratory Media Preparation Service, Vancouver, B.C., Canada, 1992 ed.

The plates were scored for colonies at day 10 and again at day 18. At day 10, CFU-E and mature BFU-E colonies were present and at day 18, primitive BFU-E, CFU-GM and CFU-GEMM colonies were present.

At day 18 50 ul of colcemid (Gibco, diluted 1/10) were evenly added to the culture dishes using an automatic pipette. The colcemid-added culture dishes were incubated for 45–60 minutes at 37° C. in 5% $CO_2$. 100 ul of hypotonic solution were added to several microfuge tubes. Colonies were pipetted from the culture dishes and individual colonies were mixed in each microfuge tube containing hypotonic solution and incubated for 20 minutes. The contents of each microfuge tube were then placed on a poly-1-lysine coated slide and incubated for 5 minutes.

20 ul of 20% fixative (3:1 methanol/acetic acid) was then added to each slide. The slides where then immersed in two changes of 5 minutes each of full strength fixative, followed by drying at 37° C. overnight.

The cultured cells were then analyzed by FISH using the Y-chromosome probes DYZ1/DYZ3 (Oncor, Inc.) in accordance with the FISH protocol published and distributed as of the date of this application by Oncor, Inc. for use with the Oncor, Inc. FISH kit. The results of FISH analysis are detailed in Table 5, below:

TABLE 5

| Slide No. | Colony Type | Slide Date | Y Signal | Metaphase (No. Cells) | Mitotic Index (%) | Total Cells |
|---|---|---|---|---|---|---|
| CS1/P1/T1 | Red | 1/30/95 | 0 | 0 | 0.00 | 158 |
| CS1/P1/T1 | Myeloid | 1/30/95 | 5 | 1 | 0.21 | 476 |
| CS2/P1/T1 | Mixed | 1/30/95 | 0 | 3 | 0.78 | 383 |
| CS2/P2/T1 | Red | 1/30/95 | 0 | 3 | 2.8 | 107 |
| CS3/P1/T2 | Myeloid | 1/30/95 | 2 | 1 | 0.26 | 380 |
| CS3/P1/T3 | Mixed | 1/30/95 | 0 | 17 | 5.25 | 324 |
| CS3/P2/T2 Control | Red | 1/30/95 | 0 | 4 | 0.52 | 644 |
| CFS100/F6 | Cytospin | 11/29/94 | 495 | | 98.61 | 502 |

Sister cells obtained from one subject (CS3) to those cultured and analyzed by FISH, as summarized in Table 5, above, were enriched and cultured in accordance with the above-described protocol. Twelve colonies were harvested on day 18 of culture from the sister cell line. PCR testing for Y-sequences in the CFS-eluates was conducted with SRY2 and SRY3 primers, each consisting of a 258 base pair sequence in SRY conserved motif. PCR was conducted in accordance with Perkin-Elmer's published PCR protocol, hereby incorporated by reference. Lanes 3 and 19 contained a 123 base pair marker. The presence of SRY-positive fetal cells in two colonies, 6 and 8, of the twelve colonies was confirmed by PCR. The presence of two positive colonies in twelve total colonies represents an enrichment level of 1 in 6, or 16.67%. The results of the PCR are summarized in Table 6, below:

TABLE 6

| Lane | Sample ID | SRY Band | Sex Indicated |
|---|---|---|---|
| 2 | CS3-2 Tube 1 | – | F |
| 4 | CS3-2 Tube 2 | – | F |
| 5 | CS3-2 Tube 3 | – | F |

TABLE 6-continued

| Lane | Sample ID | SRY Band | Sex Indicated |
|---|---|---|---|
| 6 | CS3-2 Tube 4 | + | M |
| 7 | CS3-2 Tube 5 | − | F |
| 8 | CS3-2 Tube 6 | + | M |
| 9 | CS3-2 Tube 7 | − | F |
| 10 | CS3-2 Tube 8 | − | F |
| 11 | CS3-2 Tube 9 | − | F |
| 12 | CS3-2 Tube 10 | − | F |
| 13 | CS3-2 Tube 11 | − | F |
| 14 | CS3-2 Tube 12 | − | F |
| 15 | Male Control |  | M |
| 16 | Blank | − | na |
| 17 | Female Control | − | F |
| 18 | No DNA | − | na |

Finally, both the ammonia lysis and complement lysis procedures may be carried out in solution, as described above, or may be carried out using negative selection non-rare cell binding immobilization media, such as LEUKOSORB A and LEUKOSORB B (Pall Corporation). As described more fully in the Twitty, et al. patent application, incorporated herein by reference, LEUKOSORB A and LEUKOSORB B have binding affinities primarily for nucleated cells, but not mature enucleated erythroid cells. Thus, the complement lysing step, describe above, will first be applied to rid the matrix of bound unwanted cells, then the ammonium lysis step will be carried out on an affinity medium having a binding affinity for nucleated cell populations. The wanted cells are then removed from the matrix by increasing the salt concentration or with proteases.

The adjunct use of adsorption-filtration affinity matrices as solid phase supports for ammonium lysis and complement lysis, entails layering a CFS-separated fraction onto a fibrous adsorption-filtration filter medium having a nominal pore size of about 8 microns and being capable of 40–80% leukocyte immobilization, with a 70–80% post-wash leukocyte retention rate, and which is extremely hydrophilic, being capable of wetting with solutions having surface tensions of up to 85–90 dynes, which has a hold up volume of 40–70 µl/cm$^2$ for a single layer of adsorption-filtration filter medium and which is characterized by low to medium protein binding. The preferred adsorption-filtration separation filter medium is that sold by Pall Corporation under the trademarks "LEUKOSORB" TYPES A and B or that described in U.S. Pat. Nos. 4,923,620, 4,925,572, or European Patent No. 313348, each of which is hereby incorporated by reference.

Turning now to FIGS. 5–8, there is disclosed the use of at least one leukocyte-depleting matrix which preferentially captures leukocytes by at least one of adsorption, filtration and affinity as described in U.S. Pat. No. 4,925,572 or PCT Publication No. WO 94/17209, incorporated herein by reference. The preferable leukocyte-depleting matrices are "LEUKOSORB A" and "LEUKOSORB B" both manufactured and sold by Pall Corporation. For purposes of illustration only, the leukocyte-depleting matrices depicted in FIGS. 5–8 are identified by LEUKOSORB A and LEUKOSORB B, but any type of adsorption, filtration or affinity matrix which functions to preferentially pass nucleated red blood cells or white blood cells and red blood cells in a manner as described in FIGS. 6–9 is contemplated as being useful.

Figure 5:
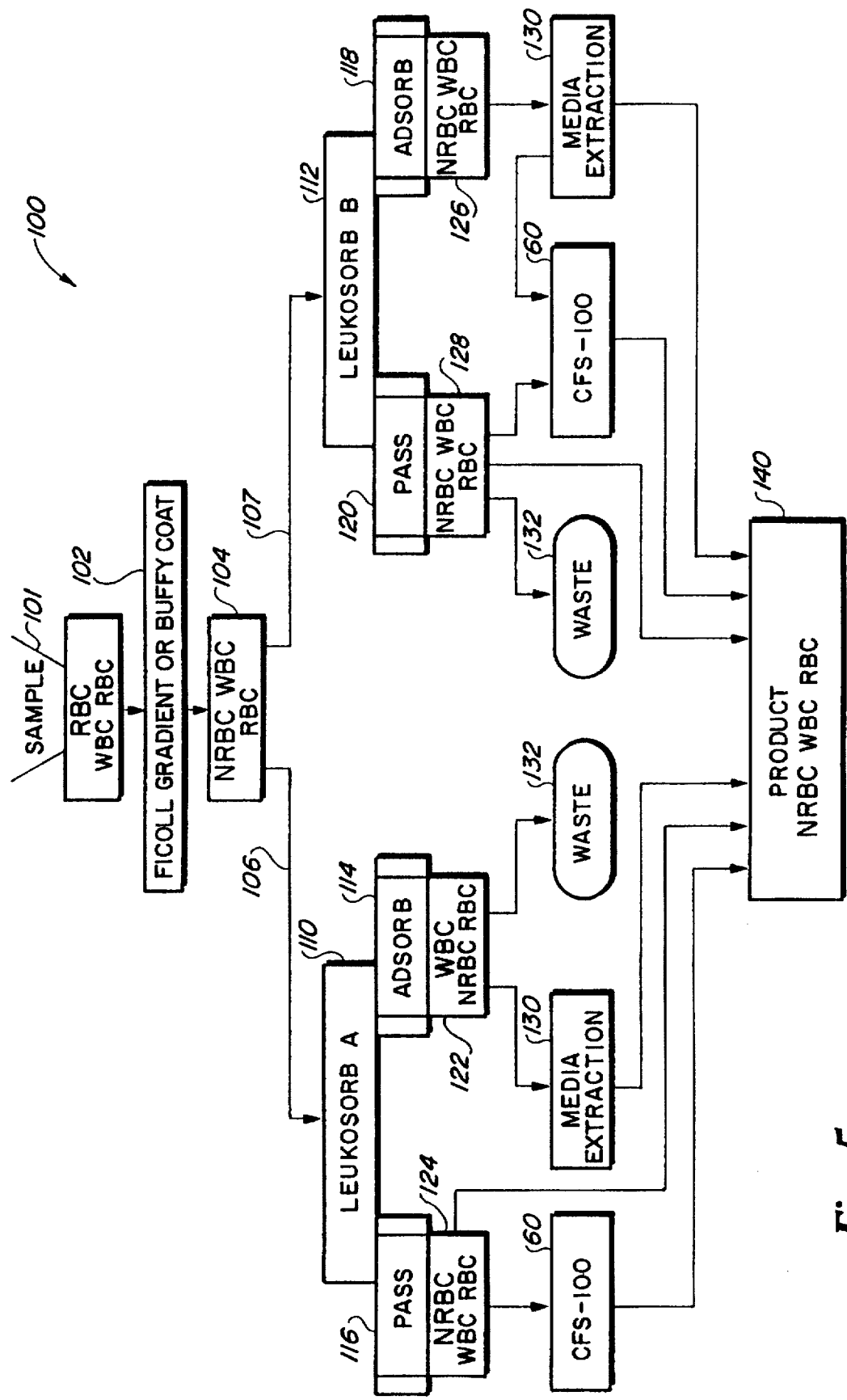
FIG. 5 is a flow diagram illustrating a first embodiment of the adjunct adsorption-filtration supports in accordance with of the present invention.

FIG. 5 illustrates a first embodiment 100 of the adsorption-filtration process in accordance with the present invention. A whole blood sample containing erythrocytes (RBC), leukocytes (WBC) and nucleated erythrocytes (NRBC) is layered onto a Ficoll gradient 102 as described earlier. Density gradient centrifugation on the Ficoll gradient separates a major fraction containing NRBC and WBC with few RBC components 104. The NRBC/WBC fraction is passed 106, 108 either over a LEUKOSORB A 110 or a LEUKOSORB B 112 adsorption-filtration medium. Passing the NRBC/WBC fraction 104 over the LEUKOSORB A 110 in step 106, passes 116 a fraction which includes a major fraction of NRBC 124 and an accompanying minor fraction of WBC and RBC, while a major fraction of WBC 122 and an accompanying minor fraction of NRBC and RBC 122 is adsorbed 114 on the LEUKOSORB A 110. Alternatively, in step 108, the NRBC/WBC fraction 104 may be passed over a LEUKOSORB B 112 medium, and a fraction of NRBC, WBC and RBC 128 is passed, while a major fraction of NRBC and WBC 126, with an accompanying minor fraction of RBC is adsorbed.

The NRBC fraction 124 from step 106 is then passed through the CFS 60, described above, to further concentrate the desired rare cell population product 140. Further, the adsorbed fraction 130 may be extracted 130 by desorbing with an extraction medium appropriate for the adsorbed cell population to yield the desired cell population product 140.

Alternatively, if step 108 is followed, the fraction 128 passing through the LEUKOSORB 112 is either discarded as waste 132 or is concentrated by CFS 60, as described above. The adsorbed fraction 126 may be desorbed 130 to yield the desired cell population product 140, or concentrated by CFS 60, as described above, to yield the desired cell population product 140.

It is to be noted that in the FIGS. 5–8, major fractions are denoted by larger typeface legends and minor fractions are denoted by smaller typeface legends. Thus, for example, in FIG. 5, the whole blood sample 100 contains a major fraction of erythrocytes (RBC) and minor fractions of leukocytes (WBC) and nucleated erythrocytes (NRBC). After the density gradient centrifugation at step 102, the fraction containing a major fraction of nucleated erythrocytes (NRBC) and leukocytes (WBC) and a minor fraction of erythrocytes (RBC) is recovered. Thus, density gradient centrifugation removes a major fraction of erythrocytes and passes the minor fraction of WBC and NRBC.

Figure 6:
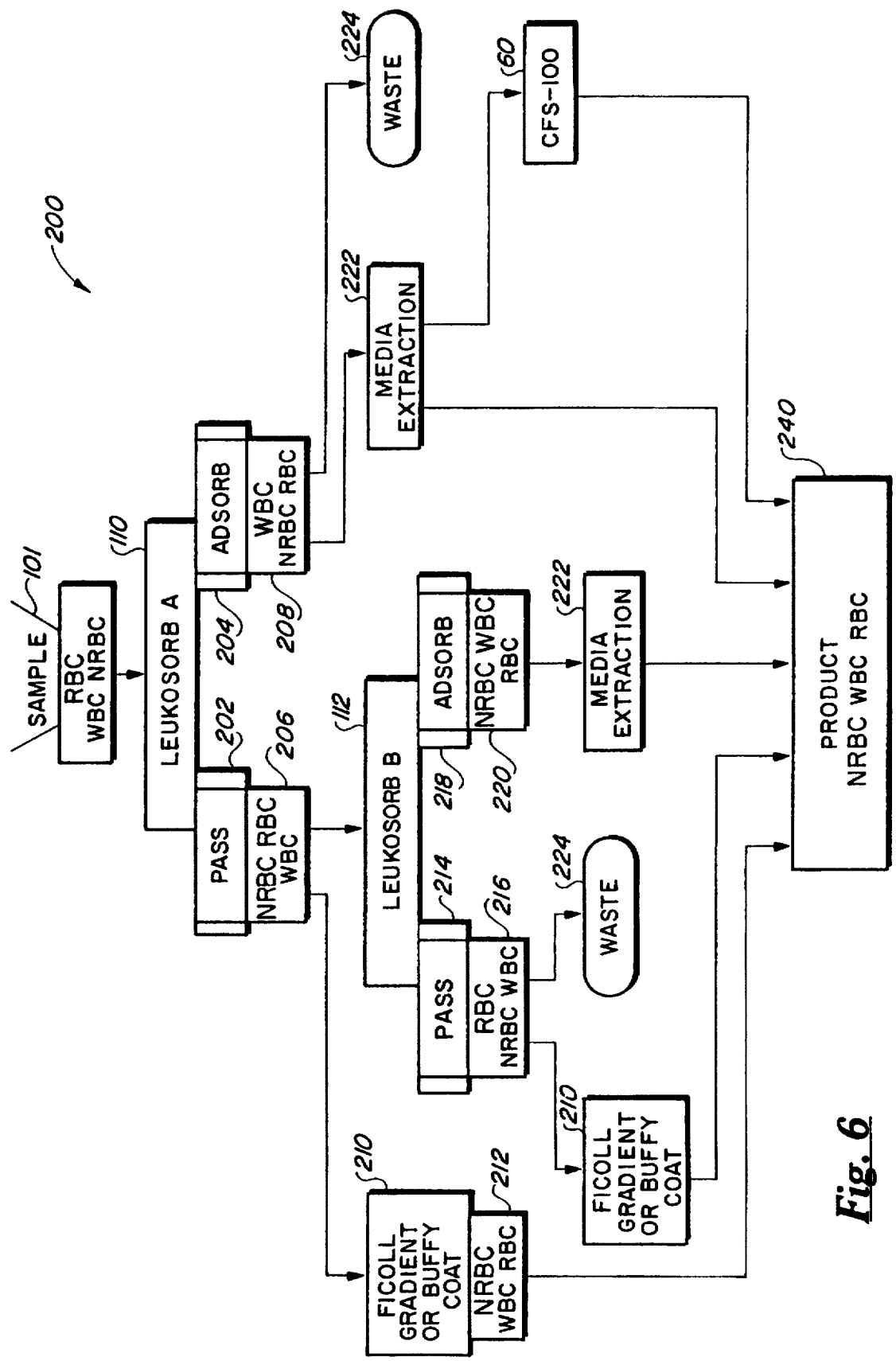
FIG. 6 is a flow diagram illustrating a second embodiment of the adjunct adsorption-filtration supports in accordance with of the present invention.
Figure 7:
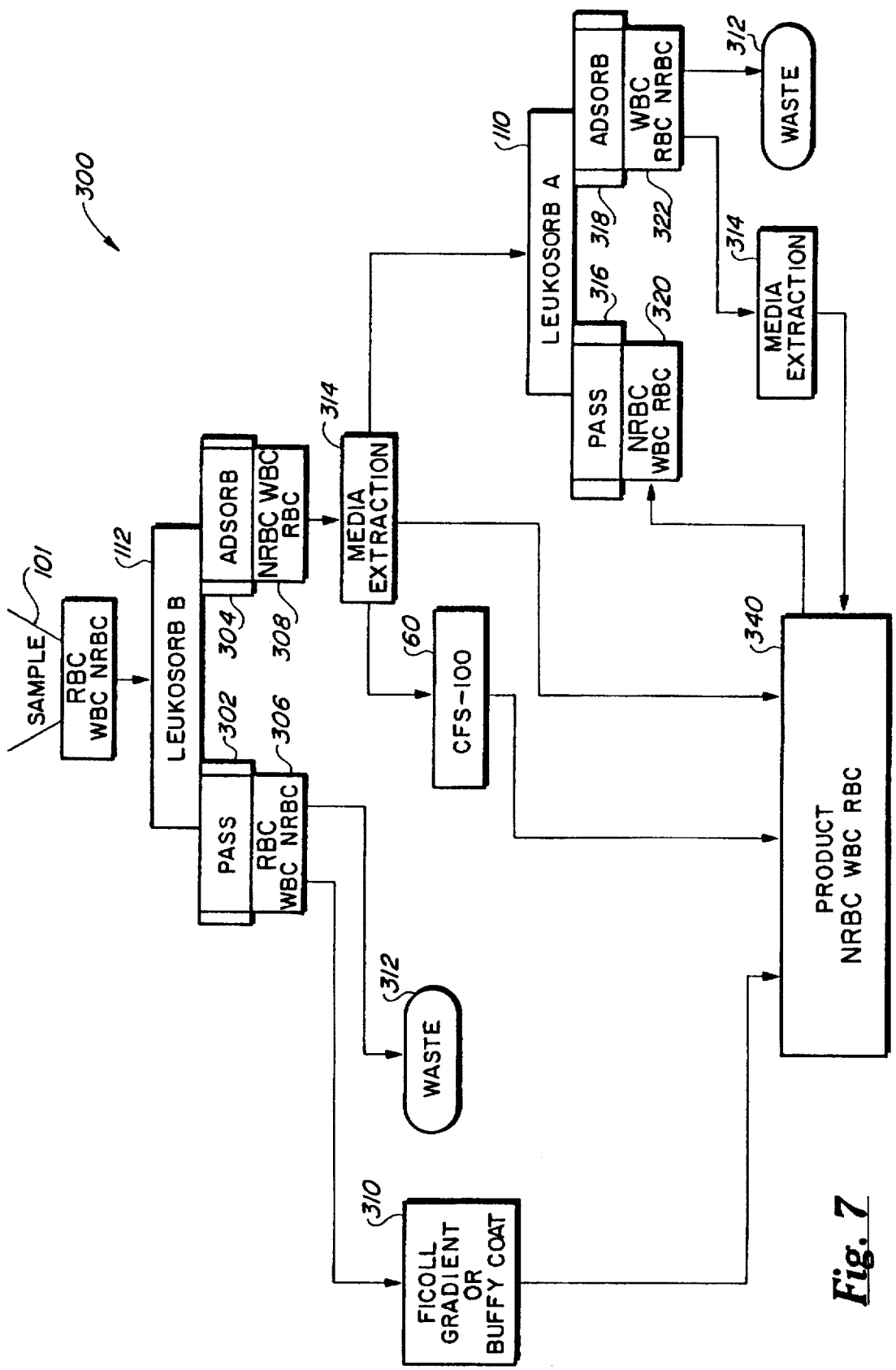
FIG. 7 is a flow diagram illustrating a third embodiment of the adjunct adsorption-filtration supports in accordance with of the present invention.
Figure 8:
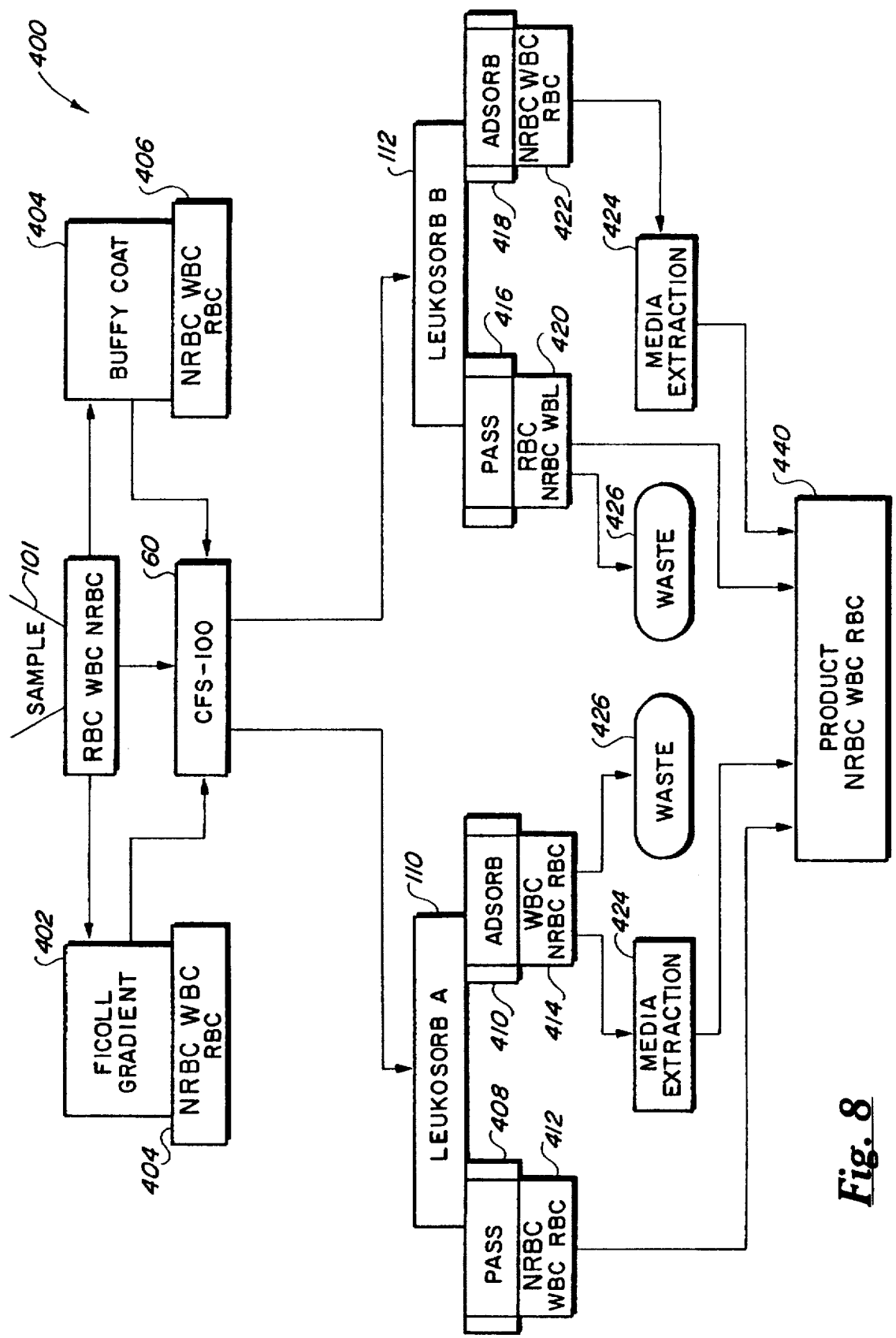
FIG. 8 is a flow diagram illustrating a fourth embodiment of the adsorption-filtration supports used as an adjunct to the enrichment method of the present invention.

FIGS. 6–8, set forth a second embodiment of the adsorption-filtration process 200, a third embodiment of the adsorption-filtration process 300, and a fourth embodiment of the adsorption-filtration process 400, respectively. In each of embodiment 200, 300 and 400, the basic process steps are identical, except that the order of performing the process steps has been altered between the embodiments as illustrated in the Figures. For example, in FIG. 6, the sample is placed onto a LEUKOSORB A medium 110, then passed either to a Ficoll gradient for density gradient centrifugation and separation of the desired cell population, or the fraction passing is placed onto a LEUKOSORB B medium 112, and the fraction passing is subject to density gradient centrifugation 210 to yield the product 240. The adsorbed fraction on the LEUKOSORB B medium 112, is extracted 222 to yield the desired product 240. The fraction adsorbed on the LEUKOSORB A medium 110 is extracted 222, and may be concentrated by CFS 60, to yield the desired cell population 240.

In FIG. 7, the sample is placed onto a LEUKOSORB B medium 112, the fraction passed is subjected to density gradient centrifugation 310 or is waste 312, while the adsorbed fraction 304 is extracted 314 and subjected to CFS 60 to yield the product 340, or the extracted fraction is passed onto LEUKOSORB A medium 100 for further adsorption 318 or filtration 316 to either positively or negatively select the desired product 340.

Finally, in FIG. 8, as illustrated in the Example set forth above, the sample either first subjected to CFS 60, or is subjected to density gradient centrifugation 404 followed by CFS 60. The concentrated sample from CFS 60, is then passed onto either LEUKOSORB A medium 110 and LEUKOSORB B medium 112, each either positively (passing) or negatively (adsorbing) the desired cell population 440.

It has been found that enrichment of rare fetal nucleated red cells from a maternal whole blood sample using Ficoll/Hypaque-1119 followed by charge flow separation yielded rare cell populations at a level between 2–7%. By using the subsequent steps of ammonium lysis followed by complement lysis, the system and method of the present invention further increased rare cell population yield to a level up to about 17%. These levels of enrichment represent substantial and significant advances in recovery of rare cell populations from the peripheral blood circulation and achieve, for the first time, sufficient numbers of separated rare cells to make clinical diagnosis possible and meaningful.

Those skilled in the art will appreciate, from the foregoing, that while the present invention has been described with reference to its preferred embodiments, that the spirit and scope of the present invention is not intended to be limited thereto, but by the claims appended hereto.

What is claimed:

1. A method for enriching a maternal whole blood sample for desired fetal cell populations within the maternal whole blood sample, comprising the steps of:
   a) density gradient centrifugation of the maternal whole blood sample in the presence of a Ficoll gradient having a density of at least about 1.119 g/ml at less than or equal to about 500 g;
   b) recovering a desired fraction containing fetal cell population from the density gradient centrifugation and passing the desired fraction containing fetal cell population through a counterflow stabilized charge-flow separator apparatus, in which the mobility of each cellular component in the maternal blood sample in the presence of an applied electrical field is opposed by a buffer counterflow, thereby concentrating desired fraction containing fetal cell population;
   c) retrieving at least one fraction eluting from the charge-flow separator apparatus having a concentrated desired fraction containing fetal cell population from step (b);
   d) depleting unwanted cells from the concentrated desired fraction containing fetal cell population; and
   e) recovering an enriched desired fetal cell population for analysis.

2. The method of claim 1 further comprising the step of obtaining a separated cell population of fetal nucleated blood cells from the charge-flow separator apparatus and passing the separated cell population of fetal nucleated blood cells through a leukocyte depleting affinity matrix.

3. The method of claim 1 further comprising the step of obtaining a separated cell population of fetal nucleated blood cells from the charge-flow separator apparatus and passing the separated cell population of fetal nucleated blood cells through a leukocyte depleting adsorption-filtration matrix.

4. The method of claim 1, wherein said step of depleting unwanted cells further comprises the step of ammonium lysis under conditions which lyse a substantial quantity of enucleate erythrocytes and without lysing substantial quantities of the desired fetal cell population.

5. The method of claim 4, wherein said step of depleting unwanted cells further comprises the step of complement lysis after the step of ammonium lysis under conditions which lyse a substantial quantity of lymphoid and myeloid cells and without lysing substantial quantities of the desired fetal cell population.

6. A method for recovering a desired fetal cell population from a maternal whole blood sample, comprising the steps of:
   a) depleting a major fraction of unwanted cells from the maternal whole blood sample, thereby concentrating a desired fetal cell population;
   b) passing the concentrated desired fetal cell population through a counterflow stabilized charge-flow separator apparatus, in which the mobility of each cellular component in the depleted blood sample in the presence of an applied electrical field is opposed by a buffer counterflow, thereby concentrating the desired fetal cell population from other cellular blood components;
   c) retrieving at least one fraction eluting from the charge-flow separator apparatus having a concentrated desired fetal cell population; and
   d) recovering an enriched desired fetal cell population for analysis.

7. The method of claim 6, wherein said step of depleting a major fraction of unwanted blood cells further comprises the step of ammonium lysis under conditions which lyse a substantial quantity of enucleate erythrocytes and without lysing substantial quantities of the desired fetal cell population.

8. The method of claim 7, wherein said step of depleting a major fraction of unwanted blood cells further comprises the step of complement lysis after the step of ammonium lysis under conditions which lyse a substantial quantity of lymphoid and myeloid cells and without lysing substantial quantifies of the desired fetal cell population.

9. The method of claim 7, wherein said step of depleting a major fraction of unwanted blood cells further comprises the step of adsorbing the desired fetal cell population onto an solid adsorption matrix having a greater binding affinity for the desired fetal cell population than for the unwanted cell populations in the maternal whole blood sample.

10. The method of claim 7, wherein said step of depleting a major fraction of unwanted blood cells further comprises the step of adsorbing the unwanted cell populations onto a solid-phase adsorption matrix having a greater binding affinity for the unwanted cell populations in the maternal whole blood sample than for the desired fetal cell population.

* * * * *